US009675444B2

(12) United States Patent
Blum et al.

(10) Patent No.: US 9,675,444 B2
(45) Date of Patent: Jun. 13, 2017

(54) HERMETICALLY SEALED IMPLANTABLE OPHTHALMIC DEVICES AND METHODS OF MAKING SAME

(71) Applicant: Elenza, Inc., Roanoke, VA (US)

(72) Inventors: Ronald D. Blum, Roanoke, VA (US); Amitava Gupta, Roanoke, VA (US); Jean-Noel Fehr, Bern (CH); Jean-Christophe Roulet, Bern (CH); Urban Schnell, Bern (CH); Walter Doll, Bern (CH); Roland Michaely, Bern (CH)

(73) Assignee: ELENZA, INC., Roanoke, VA (US)

( * ) Notice: Subject to any disclaimer, the term of this patent is extended or adjusted under 35 U.S.C. 154(b) by 57 days.

(21) Appl. No.: 14/657,519

(22) Filed: Mar. 13, 2015

(65) Prior Publication Data

US 2015/0182331 A1    Jul. 2, 2015

Related U.S. Application Data

(62) Division of application No. 13/812,226, filed as application No. PCT/US2011/045188 on Jul. 25, 2011, now Pat. No. 8,992,610.
(Continued)

(51) Int. Cl.
| | | |
|---|---|---|
| *H05K 3/30* | (2006.01) | |
| *A61F 2/16* | (2006.01) | |

(Continued)

(52) U.S. Cl.
CPC .............. *A61F 2/1624* (2013.01); *A61F 2/14* (2013.01); *G02F 1/1341* (2013.01); *H05K 3/301* (2013.01);
(Continued)

(58) Field of Classification Search
CPC ...... H05K 7/1431; H05K 1/14; H01R 12/716; H01K 3/366; Y10T 29/49117;
(Continued)

(56) References Cited

U.S. PATENT DOCUMENTS

| | | |
|---|---|---|
| 4,300,818 A | 11/1981 | Schachar |
| 4,309,603 A | 1/1982 | Stauffer |

(Continued)

FOREIGN PATENT DOCUMENTS

| | | |
|---|---|---|
| EP | 1 674 049 A1 | 6/2006 |
| WO | WO-97/48004 A1 | 12/1997 |
| WO | WO-2006/050366 A2 | 5/2006 |

OTHER PUBLICATIONS

International Preliminary Report on Patentability issued in International Application No. PCT/US2011/045188 mailed Feb. 7, 2013.
(Continued)

*Primary Examiner* — Peter DungBa Vo
*Assistant Examiner* — Azm Parvez
(74) *Attorney, Agent, or Firm* — Foley & Lardner LLP

(57) ABSTRACT

Many modern implantable ophthalmic devices include electronic components, such as electro-active cells, that can leak harmful substances into the eye and/or surrounding tissue. In the implantable ophthalmic devices disclosed herein, electronic components are hermetically sealed within cavities formed by bonding together two or more glass wafers. Bonding the glass wafers together with laser fusion bonding, pressure bonding, or anodic bonding creates a seal that leaks at a rate of less than about $5\times10^{-12}$ Pa m$^3$s$^{-1}$ when subjected to a helium leak test. Hermetically sealed feedthroughs formed of conductive material running through channels in the wafers provide electrical connections to components inside the sealed cavities. In some cases, the conductive material has a coefficient of thermal expansion (CTE) that is
(Continued)

roughly equal to (e.g., within 10% of) the CTE of the glass wafers to minimize leakage due to thermally induced expansion and contraction of the conductive material and the glass wafer.

20 Claims, 14 Drawing Sheets

Related U.S. Application Data

(60) Provisional application No. 61/367,511, filed on Jul. 26, 2010, provisional application No. 61/367,956, filed on Jul. 27, 2010, provisional application No. 61/380,340, filed on Sep. 7, 2010, provisional application No. 61/382,041, filed on Sep. 13, 2010.

(51) Int. Cl.
    A61F 2/14       (2006.01)
    G02F 1/1341     (2006.01)
    H05K 3/36       (2006.01)
    A61F 2/48       (2006.01)
    H01L 23/15      (2006.01)
    H01L 23/538     (2006.01)

(52) U.S. Cl.
    CPC ............. H05K 3/36 (2013.01); A61F 2/1613 (2013.01); A61F 2002/482 (2013.01); A61F 2240/001 (2013.01); A61F 2250/0069 (2013.01); H01L 23/15 (2013.01); H01L 23/5389 (2013.01); Y10T 29/49126 (2015.01)

(58) Field of Classification Search
    CPC ......... Y10T 29/49204; Y10T 29/49128; Y10T 29/49208
    USPC ................................ 29/830, 829, 825, 592.1
    See application file for complete search history.

(56) References Cited

U.S. PATENT DOCUMENTS

| | | |
|---|---|---|
| 4,333,720 A | 6/1982 | Suzuki et al. |
| 4,373,218 A | 2/1983 | Schachar |
| 4,466,703 A | 8/1984 | Nishimoto |
| 4,601,545 A | 7/1986 | Kern |
| 4,787,903 A | 11/1988 | Grendahl |
| 5,066,301 A | 11/1991 | Wiley |
| 5,108,427 A | 4/1992 | Majercik et al. |
| 5,653,751 A | 8/1997 | Samiy et al. |
| 5,712,721 A | 1/1998 | Large |
| 5,750,926 A * | 5/1998 | Schulman ............ A61N 1/3754 174/564 |
| 6,200,342 B1 | 3/2001 | Tassignon |
| 6,282,449 B1 | 8/2001 | Kamerling et al. |
| 6,619,799 B1 | 9/2003 | Blum et al. |
| 6,638,304 B2 | 10/2003 | Azar |
| 6,667,471 B2 | 12/2003 | Bos et al. |
| 6,706,066 B1 | 3/2004 | Zhou et al. |
| 6,790,232 B1 | 9/2004 | Lang |
| 7,041,133 B1 | 5/2006 | Azar |
| 7,647,836 B2 * | 1/2010 | O'Brien ................ G01L 9/0042 73/756 |
| 7,926,940 B2 | 4/2011 | Blum et al. |
| 7,964,833 B2 | 6/2011 | Holladay |
| 8,215,770 B2 | 7/2012 | Blum et al. |
| 8,763,245 B1 * | 7/2014 | Lucisano ................ H01L 23/10 29/842 |
| 2003/0089394 A1 | 5/2003 | Chang-Chien et al. |
| 2004/0183965 A1 | 9/2004 | Lundgren |
| 2004/0233383 A1 | 11/2004 | Sandler et al. |
| 2005/0202591 A1 | 9/2005 | Chen et al. |
| 2006/0038288 A1 | 2/2006 | Yoshioka et al. |
| 2006/0095128 A1 | 5/2006 | Blum et al. |
| 2006/0113054 A1 | 6/2006 | Silvestrini |
| 2006/0122531 A1 | 6/2006 | Goodall et al. |
| 2006/0164593 A1 | 7/2006 | Peyghambarian et al. |
| 2006/0206205 A1 | 9/2006 | Azar |
| 2007/0084270 A1 | 4/2007 | Jarrett |
| 2007/0261497 A1 | 11/2007 | O'Brien et al. |
| 2009/0033863 A1 | 2/2009 | Blum et al. |
| 2010/0112195 A1 | 5/2010 | Kodas et al. |
| 2010/0121443 A1 | 5/2010 | Michel et al. |

OTHER PUBLICATIONS

International Search Report and Written Opinion received in connection with international application No. PCT/US2011/045188 dtd Dec. 7, 2011.

Notice of Allowance dated Nov. 24, 2014 in U.S. Appl. No. 13/812,226.

Office Action dated Jul. 11, 2014, in corresponding Argentenian Appln. No. P080100772, 6 pages.

Office Action dated Jul. 23, 2014 in corresponding Korean Application No. 10-2009-7016885, and English translation, 4 pages.

Office Action in U.S. Appl. No. 12/035,779 dated Apr. 8, 2011.

Office Action issued in Japanese Application No. 2011-500930 mailed May 28, 2013.

Search Report received in European Patent Application No. 08 73 0512.4 dated Nov. 7, 2012.

\* cited by examiner

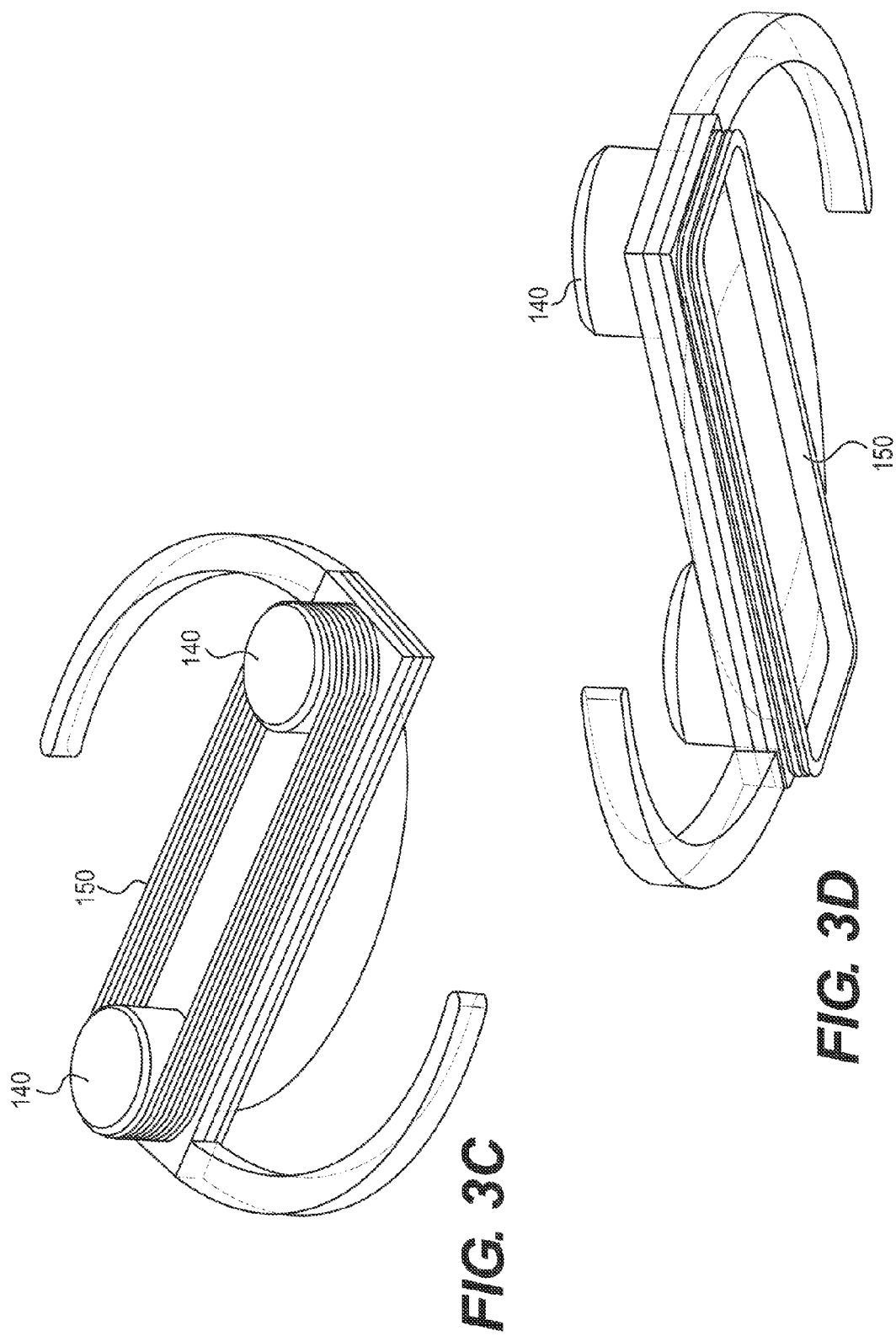

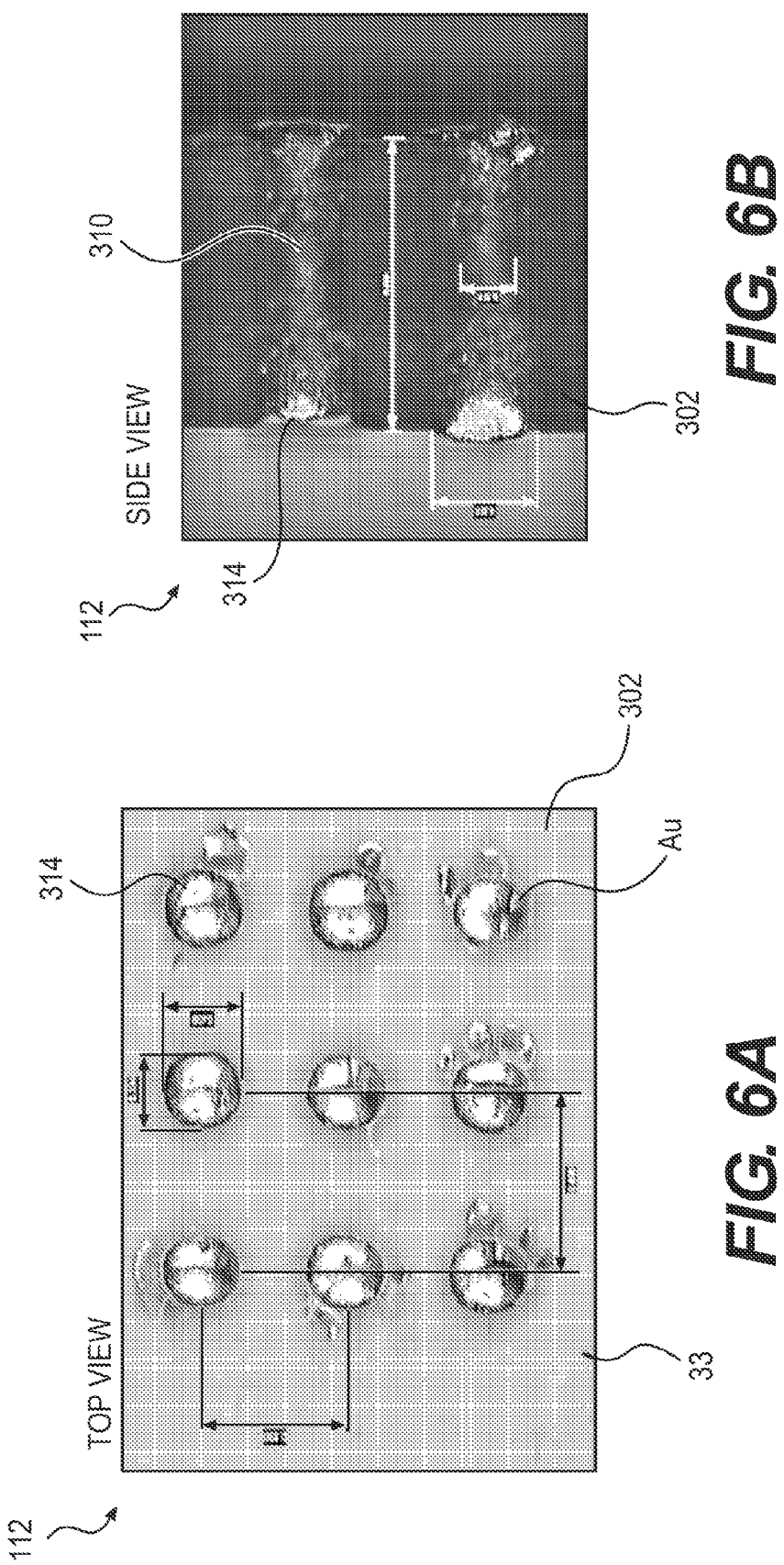

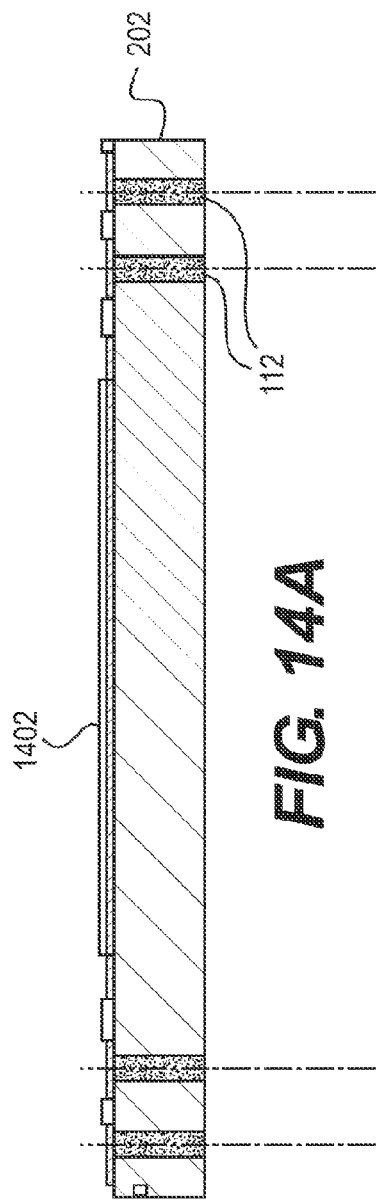
FIG. 14A
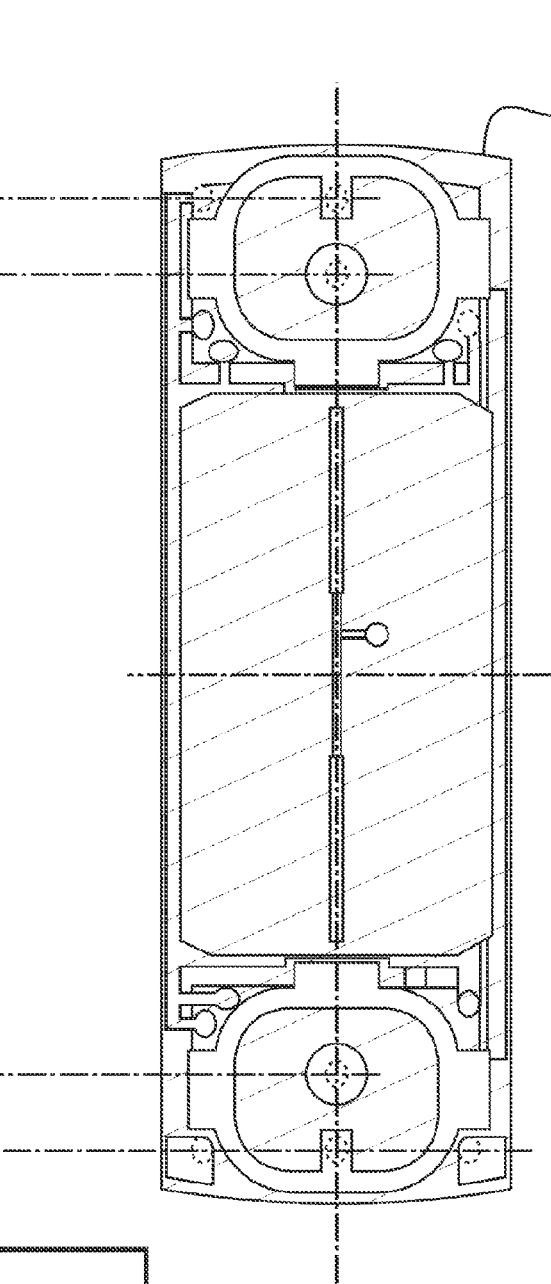
FIG. 14B
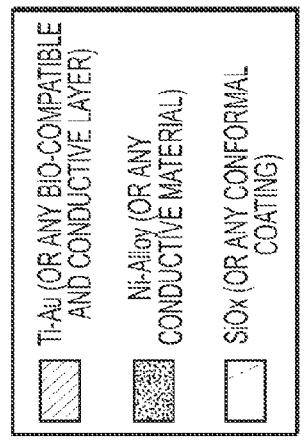

HERMETICALLY SEALED IMPLANTABLE OPHTHALMIC DEVICES AND METHODS OF MAKING SAME

CROSS-REFERENCE TO RELATED PATENT APPLICATIONS

The present application is a division of U.S. patent application Ser. No. 13/812,226, filed Apr. 4, 2013, which is a National Stage of International Application No. PCT/US2011/045188 filed on Jul. 25, 2011, International Application No. PCT/US2011/045188 claims the benefit of: U.S. Provisional Application 61/367,511, filed Jul. 26, 2010, and entitled "Intraocular Implant with Hermetically Sealed Liquid Crystal Cell"; U.S. Provisional Application 61/367,956, filed Jul. 27, 2010, and entitled "Intraocular Implant with Hermetically Sealed Liquid Crystal Cell with Dynamic Diffractive Lens and/or Dynamic Refractive Lens and/or Dynamic Aperture"; U.S. Provisional Application 61/380,340, filed Sep. 7, 2010, and entitled "Hermetically Sealed Feed-Throughs to Establish Electrical Connection through Thin Glass Wafers"; and U.S. Provisional Application 61/382,041, filed Sep. 13, 2010, and entitled "Low Temperature Glass to Glass Anodic Bonding." Each of the above-reference applications is incorporated herein by reference in its entirety.

BACKGROUND

There are two major conditions that affect an individual's ability to focus on near and intermediate distance objects: presbyopia and pseudophakia. Presbyopia is the loss of accommodation of the crystalline lens of the human eye that often accompanies aging. In a presbyopic individual, this loss of accommodation first results in an inability to focus on near distance objects and later results in an inability to focus on intermediate distance objects. It is estimated that there are approximately 90 million to 100 million presbyopes in the United States. Worldwide, it is estimated that there are approximately 1.6 billion presbyopes.

The standard tools for correcting presbyopia are reading glasses, multifocal ophthalmic lenses, and contact lenses fit to provide monovision. Reading glasses have a single optical power for correcting near distance focusing problems. A multifocal lens is a lens that has more than one focal length (i.e., optical power) for correcting focusing problems across a range of distances. Multifocal optics are used in eyeglasses, contact lenses, and intraocular lenses (IOLs). Multifocal ophthalmic lenses work by means of a division of the lens's area into regions of different optical powers. Multifocal lenses may be comprised of continuous surfaces that create continuous optical power as in a Progressive Addition Lens (PAL). Alternatively, multifocal lenses may be comprised of discontinuous surfaces that create discontinuous optical power as in bifocals or trifocals. Contact lenses fit to provide monovision are two contact lenses having different optical powers. One contact lens is for correcting mostly far distance focusing problems and the other contact lens is for correcting mostly near distance focusing problems.

Pseudophakia is the replacement of the crystalline lens of the eye with an IOL, usually following surgical removal of the crystalline lens during cataract surgery. For all practical purposes, an individual will get cataracts if he or she lives long enough. Furthermore, most individuals with cataracts will have a cataract operation at some point in their lives. It is estimated that approximately 1.2 million cataract surgeries are performed annually in the United States. In a pseudophakic individual, the absence of the crystalline lens causes a complete loss of accommodation that results in an inability to focus on either near or intermediate distance objects.

Conventional IOLs are monofocal, spherical lenses that provide focused retinal images for far objects (e.g., objects over two meters away). Generally, the focal length (or optical power) of a spherical IOL is chosen based on viewing a far object that subtends a small angle (e.g., about seven degrees) at the fovea. Unfortunately, because monofocal IOLs have a fixed focal length, they are not capable of mimicking or replacing the eye's natural accommodation response. Fortunately, ophthalmic devices with electro-active elements, such as liquid crystal cells, can be used to provide variable optical power as a substitute for the accommodation of a damaged or removed crystalline lens. For example, electro-active elements can be used as shutters that provide dynamically variable optical power as disclosed in U.S. Pat. No. 7,926,940 to Blum et al., which is incorporated herein by reference in its entirety.

IOLs with electro-active elements and other electronic components must be well-sealed to prevent potentially foreign substances, such as the liquid crystal materials used in the electro-active elements, from leaking into the eye and surrounding tissue. To date, IOLs with electro-active elements and other electronic components have been made by potting or encapsulating the components in a shell of epoxy, polyurethane, or another suitable type of curable compound. Unfortunately, potting compounds do not always adhere well to the biocompatible metals used for electrical connections in IOLs. Potting compounds may also degrade over an IOL's expected lifetime, which can be twenty years or more.

Alternatively, components can be sealed between pieces of glass that are glued together. The pieces of glass are coated with adhesive, with wires for connecting the components placed on one piece of glass. Pushing together the pieces of glass deforms the wire and causes the adhesive to flow around the deformed wire. Adhesive seals can also degrade over the an IOL's expected lifetime. In addition, the adhesive does not always create a perfect seal around the deformed wire.

SUMMARY

Embodiments of the technology disclosed herein include an implantable ophthalmic device with a hermetically sealed feedthrough and a hermetically sealed cavity and a method for making such an implantable ophthalmic device. An illustrative implantable ophthalmic device includes a first substrate having a hermetically sealed feedthrough that provides a conductive path for electrical communication from a first side of the first substrate to a second side of the first substrate. The first side of the first substrate is bonded to a second substrate, e.g., using anodic or laser fusion bonding, to at least partially define a hermetically sealed cavity that contains an electronic component in electrical communication with the conductive path provided by the hermetically sealed feedthrough. When subject to a helium leak test, the hermetically sealed feedthrough and the hermetically sealed cavity leak at a rate of less than about $5 \times 10^{-12}$ Pa m$^3$s$^{-1}$.

In some embodiments, the hermetically sealed feedthrough is formed by creating a channel, whose diameter may be about 100 μm to about 250 μm, that connects the first and second sides of the first substrate. The channel is filled with an conductive material, such as titanium, nickel, gold, iron, or an alloy thereof, to provide the conductive path that links the first and second sides of the first substrate. In some cases, the conductive material has a coefficient of thermal expansion (CTE) that is approximately equal to a CTE of the first substrate, e.g., the CTEs of the conductive material and the first substrate may be about 2.0 ppm to about 5.0 ppm. The conductive material is in electrical communication with the electronic component, which may be an application-specific integrated circuit processor, capacitor, memory, programmable logic analyzer, analog-to-digital converter, or a battery charger.

An exemplary hermetically sealed feedthrough may be coated or capped with a biocompatible conductive material, such as gold, with a thickness of about 10 µm to about 200 µm and/or a resistance of about 10 Ohms or less. The biocompatible conductive material provides an electrical connection between the hermetically sealed feedthrough and an electronic component outside the hermetically sealed cavity, such as an electro-active element. In some examples, the electro-active element is made by (i) filling another cavity with liquid crystal material via a glass tube; and (ii) closing the glass tube to seal the liquid crystal material in the cavity. Alternatively, the electro-active element can be made by (i) filling a cavity with liquid crystal material via channels having modified interior surfaces, e.g., using aminosilane, silanols, and/or other hydroxysilane derivatives; and (ii) collapsing the channels to seal the liquid crystal material in the cavity.

In some devices, the first and second substrates are made of borosilicate glass, such as Borofloat® 33, and/or fused silica. Each substrate may be about 25-300 µm thick. A third substrate can be bonded to the second side of the first substrate to define the hermetically sealed cavity using laser fusion bonding, pressure bonding, or anodic bonding. One or more of the substrates may be at least partially coated with a conformal layer that is deposited about the hermetically sealed cavity to prevent leaks through cracks or fissures that may develop in the hermetically sealed cavity.

The foregoing summary is illustrative only and is not intended to be in any way limiting. In addition to the illustrative aspects, embodiments, and features described above, further aspects, embodiments, and features will become apparent by reference to the following drawings and the detailed description.

BRIEF DESCRIPTION OF THE DRAWINGS

The accompanying drawings, which are incorporated in and constitute a part of this specification, illustrate embodiments of the invention and together with the description serve to explain principles of the invention.

FIGS. 3A-3D show views of alternative coil arrangements in a hermetically sealed electronics assembly.

FIGS. 6A and 6B show, respectively, plan and elevation pictures of NiFe feedthroughs capped with gold and fabricated in Borofloat® 33 glass wafers.

FIGS. 14A and 14B show elevation and plan views, respectively, of a wafer with a conformal coating to provide protection from leaks through cracks or fissures in the hermetic seal.

DETAILED DESCRIPTION

Implantable Ophthalmic Devices with Hermetically Sealed Cavities and Feedthroughs Implantable ophthalmic devices, such as intraocular lenses, intraocular implants, corneal inlays, and corneal onlays, are typically implanted in the eye to serve as permanent or quasi-permanent correction for pseudophakia, aphakia, and other conditions affecting a patient's vision. Illustrative implantable ophthalmic devices may be inserted or implanted in the anterior chamber or posterior chamber of the eye, into the capsular sac, or the stroma of the cornea (similar to a corneal inlay), or into the epithelial layer of the cornea (similar to a corneal onlay), or within any anatomical structure of the eye. Because they are inserted or implanted into the eye itself, they should not leak or leach foreign materials, such as liquid crystal material or electrolytes used in batteries, into the eye or surrounding tissue. Otherwise, they could cause irreversible damage to the eye and/or tissue surrounding the eye.

Figure 1:
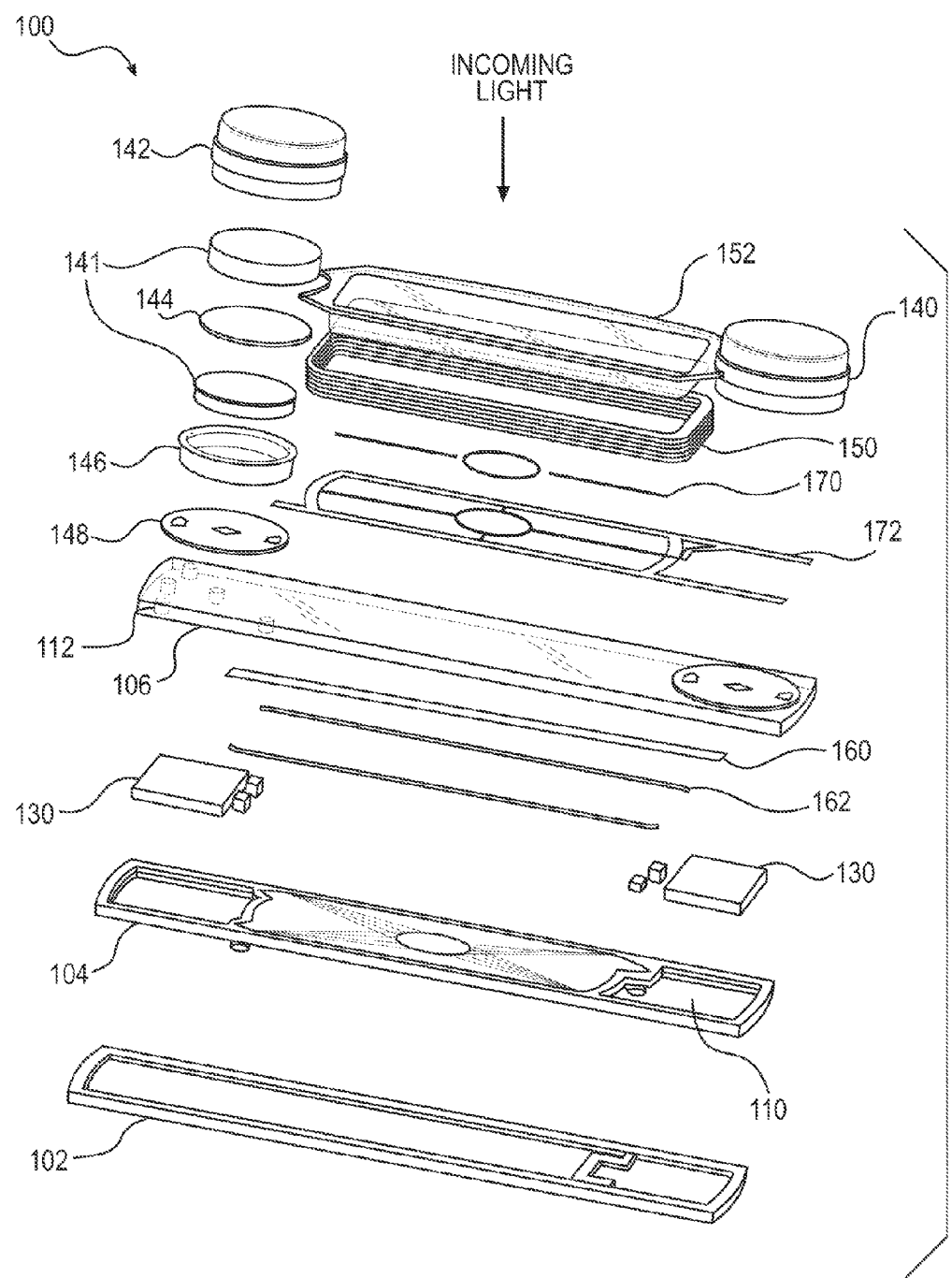
FIG. 1 is an exploded view of a hermetically sealed electronics assembly to be used in an implantable ophthalmic device.

FIG. 1 is an exploded view of an electronics assembly 100 for an exemplary implantable ophthalmic device with cavities 110 and feedthroughs 112 that are hermetically sealed to prevent leakage of foreign material from the device 100 into the eye. As defined herein, a hermetically sealed cavity or feedthrough is a cavity or feedthrough that passes an American Society for Testing and Materials (ASTM) E493/E493M-11 helium leak test with a leak rate of less than $5.0 \times 10^{-12}$ Pa m$^3$s$^{-1}$. In preferred embodiments, the amount of helium that leaks through a hermetic seal during a helium leak is undetectable, i.e., it is lower than the normal atmospheric concentration of helium.

The assembly 100 includes electronic components—in this case, application-specific integrated circuits (ASICs) 130 that have different functional blocks and may be populated with additional electronic components—disposed within the cavities 110 in an intermediate wafer 104. The ASICs 130 can be populated with subcomponents using thermo-compression bonding via TiAgNiAu pads material with mechanical tolerances of ±10 µm in all three dimensions. The assembly may also include AgPb capacitors (not shown), such as 01005 SMD surface-mount capacitors, that are bonded to a printed circuit board (PCB) (not shown) with anisotropic conductive adhesives with a lateral alignment tolerance of ±50 µm. In preferred embodiments, the total height from the surface of the PCB to the top of the capacitor is about 255±10 µm.

The cavities 110 are defined by sealing apertures in the intermediate wafer 104 between a bottom wafer 102 and a top wafer 106, which can be bonded together using laser fusion bonding, pressure bonding, and/or anodic bonding as described below. Other elements, such as an electro-active cell 160 and an obscuration 162, which comprises an opaque layer that absorbs more than 90% of incident light, may be affixed to or sealed between the wafers 102, 104, and 106, which can be made of borosilicate glass (e.g., Borofloat® 33 or D263™) pure silica ($SiO_2$), fused silica, or any other suitable material.

Figure 2A:
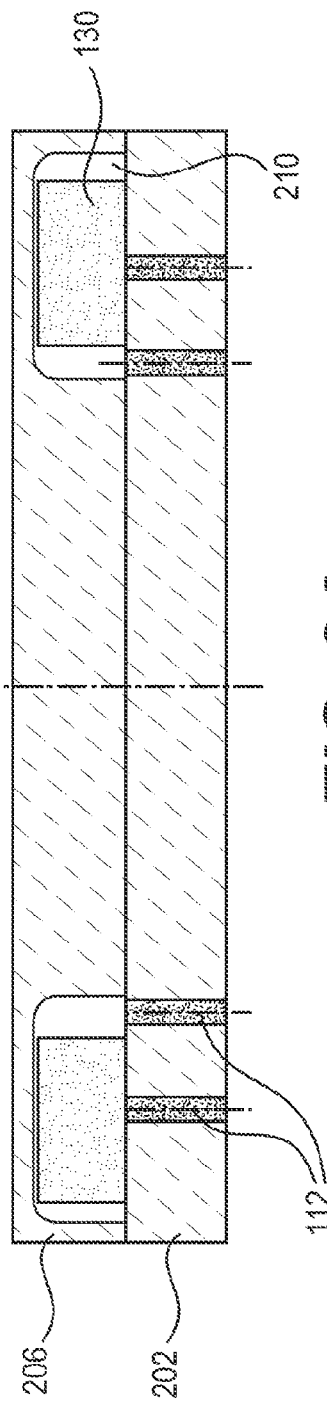
FIGS. 2A and 2B are elevation and plan views, respectively, of alternative hermetically sealed cavities formed between a pair of wafers.
Figure 2B:
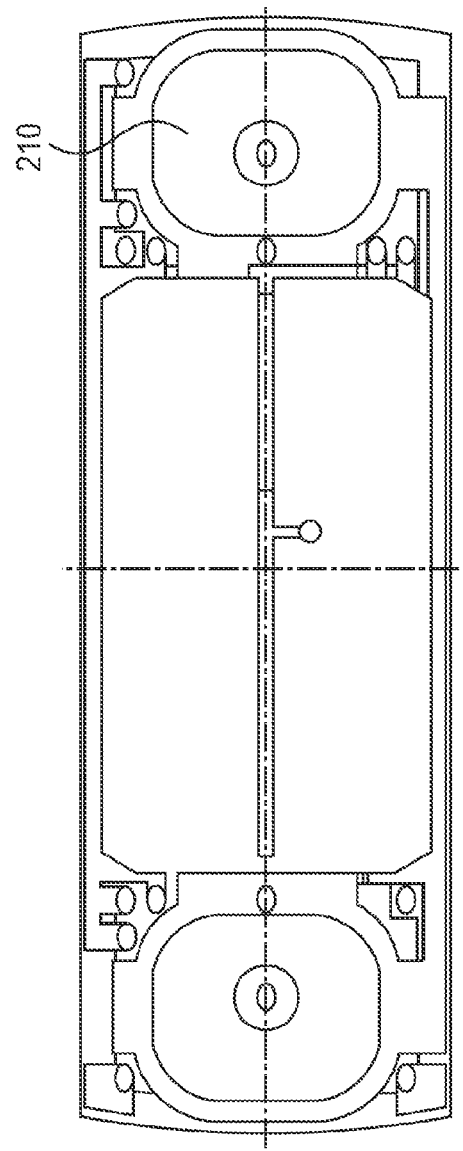

FIGS. 2A and 2B show elevation and plan views, respectively, of an alternative assembly 200 with cavities 210 formed between an alternative bottom wafer 202 and an alternative top wafer 206. Instead of defining an aperture, the top wafer 206 includes two hollows or depressions at either end. Each depression is large enough to hold an ASIC 130 and/or other electronic components. The ASIC 130 and/or other components are positioned within the depressions, and the cavities 210 are formed by bonding the bottom wafer 202 to the top wafer 206, e.g., by laser fusion bonding or anodic bonding. Hermetically sealed feedthroughs 112 provide electrical connections to the ASIC 130 and/or other electronic components in the cavities 210. Those of skill in the art will readily appreciate that other arrangements of wafers and cavities are also possible. For example, cavities may be formed between depressions in two wafers. In addition, a single wafer may include both an aperture for forming a cavity as described with respect to FIG. 1 and a depression for forming a cavity as described with respect to FIGS. 2A and 2B.

Referring again to FIG. 1, the ASICs 130 are electrically connected to batteries 140 via the feedthroughs 112 that run through the top wafer 106. The batteries 140, which may be rechargeable, include cells 141 held apart by a separator 144 and covered in a casing 142 that provides leakage protection for up to 25 years or more. A battery casing isolation ring 146 insulates the cells 141 from the rest of the assembly 100, and a battery insert plate 148 hold the battery 140 and its components in place with respect to the top wafer 106.

The assembly 100 also includes an inductive antenna coil 150 and a photovoltaic cell 170 that can be used to recharge the batteries 140. The coil 150 and the photovoltaic cell 170 can also be used for wireless communication with external processors, e.g., to update and/or extract information store in memory on one or both of the ASICs 130. The photovoltaic cell 170 can also be used to detect accommodative triggers, changes in pupil diameter, and/or other physiological or environmental indications with an average sensitivity of about 0.48 nA/lux $mm^2$. In some embodiments, the assembly 100 includes two TiAu—PIN—ZnO photovoltaic cells: a first cell with diameter of about 1.175-1.225 mm and a second cell with dimensions of about 0.1 mm×1.8 mm. In some examples, the coil 150 has about fifteen windings arranged about a perimeter of 5.7 mm×2.6 mm.

The coil 150 and photovoltaic cell 170 are also be in electrical communication with the ASICs 130 via the feedthroughs 112. For instance, a battery charger (not shown) in one of the ASICs 130 may control the recharging process as described in PCT/US2011/040896 to Fehr et al., which is incorporated herein by reference in its entirety. Similarly, a processor in one of the ASICs 130 may receive signals from the photovoltaic cell 170 representing the pupil diameter as also described in PCT/US2011/040896 to Fehr et al. The processor may also control the diameter of an aperture defined by the electro-active cell 160 in response to signals from the photovoltaic cell 170, e.g., as described in U.S. Pat. No. 7,926,940 to Blum et al., which is also incorporated herein by reference in its entirety.

Figure 3A:
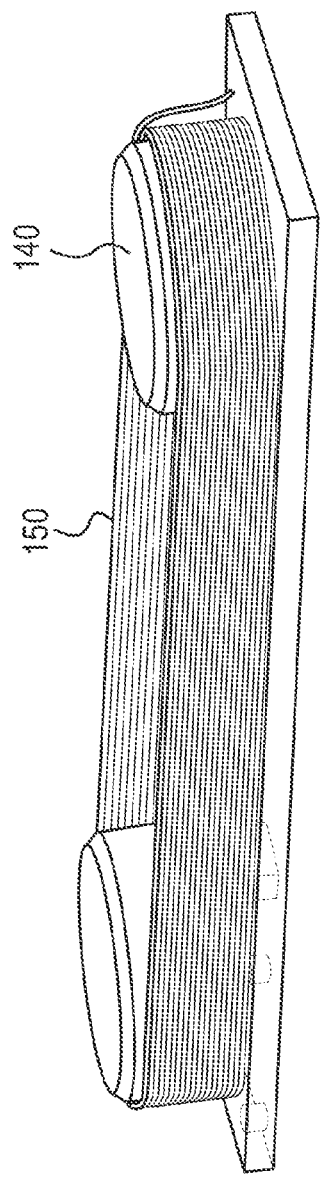

FIGS. 3A-3D show different arrangements of the coil 150 with respect to the rest of the electronics assembly. For example, the coil 150 can be wrapped around the batteries 140 as shown in FIGS. 3A and 3C. Winding the coil 150 around The batteries 140 provide good mechanical stability for the coil 150, but may impose constraints on how the implant is assembled (e.g., batteries 140 before the coil 150). The batteries 140 may also interfere with inductive coupling between the coil 150 and external electromagnetic sources (antennas).

Figure 3B:
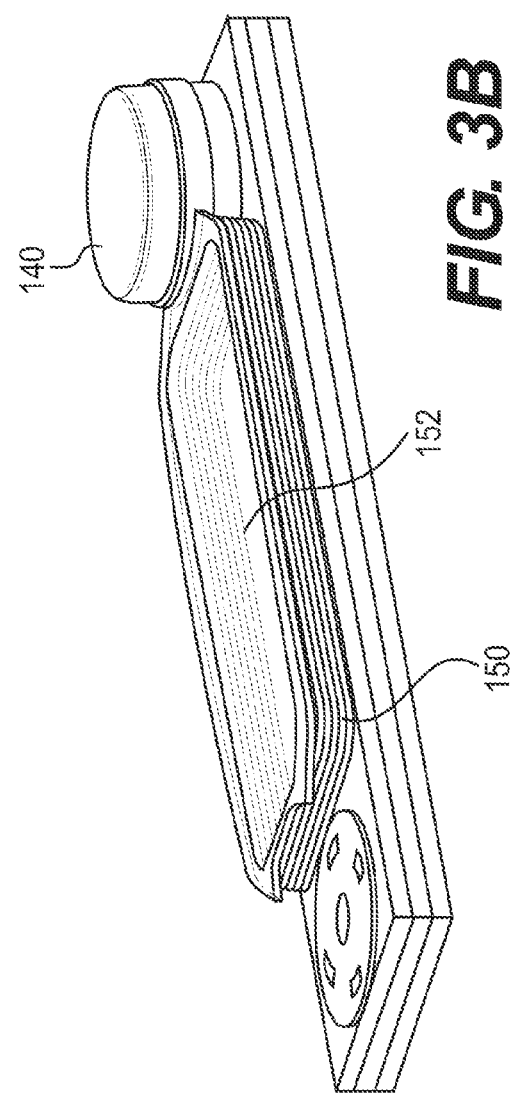

The coil 150 can also be wound around a separate support 152 as shown in FIGS. 1 and 3B. In some cases, an optic, such as an aspheric lens or a spherical lens, may be integrated into the support 152. For example, a portion of the support's outer surface may be curved or patterned to refract or diffract incident light. Using a separate support 152 also increases the flexibility of the manufacturing process by obviating any need to install certain components (e.g., batteries 140) before the coil 150. It also makes it possible to optimize the coil's coupling efficiency by allowing the coil 150 to follow a path away from potential sources of interference. However, using the separate support 152 may increase the manufacturing complexity and total mass of the implantable ophthalmic device.

Alternatively, the coil 150 may be self-sustaining, i.e., it may not require any additional support. Like other coils, self-sustaining coils should be positioned within acceptable mechanical tolerances, and may be held in place with respect to the wafers using an adhesive. Care should be taken to prevent self-sustaining coils from deforming during encapsulation of the electronics assembly 100 in acrylic, resin, or other media.

The coil 150 can be positioned on the top wafer 106 as shown in FIG. 3C to fill the space between or around the batteries 140. Alternatively, the coil 150 can be positioned on or around the bottom side of the bottom wafer 202 as shown in FIG. 3D. Mounting the coil 150 on the bottom of the bottom wafer 202 relaxes the positioning tolerances for the coil 150 and makes positioning the obscuration 162 simpler. Feedthroughs 112 running through bottom wafer 202 and/or wires running around the edge of the bottom wafer 202 connect the coil 150 to the ASIC(s) 130, batteries 140, and any other electronic components.

Figure 4A:
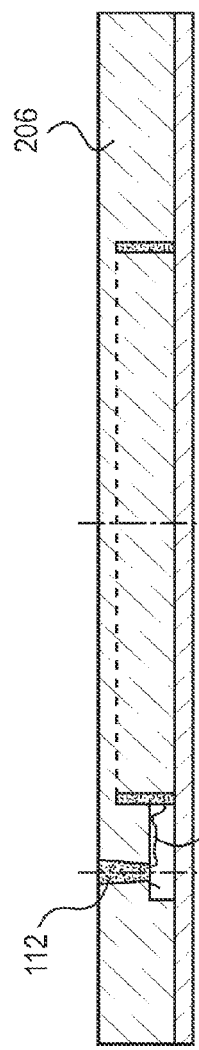
FIGS. 4A and 4B show, respectively, elevation and plan views of a coil disposed within a hermetically sealed cavity.
Figure 4B:
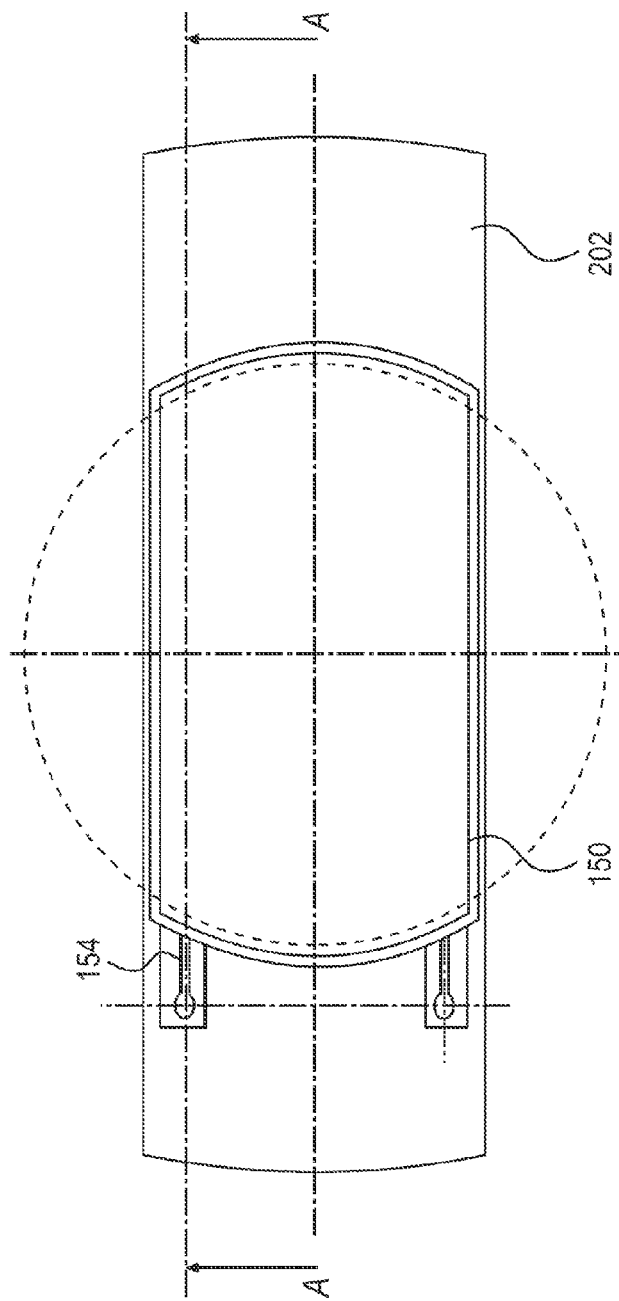

The coil 150 can also be sealed within a cavity to eliminate the need for feedthroughs between the coil 150 and the ASICs 130 as shown in FIGS. 4A and 4B. In this example, the coil 150 is embedded inside a 0.3 mm thick glass "disc" with two electrical connection on one side of the "disc". Because the coil 150 is hermetically sealed within the cavity, non-biocompatible material can be used for the coil wires (e.g. copper instead of gold) and for the insulation layer. Sealing the coil 150 within a cavity also eliminates the need to use biocompatible conductive materials to connect the coil 150 to components within the cavity.

The coil 150 can be sealed within a cavity as follows. First, a deep cavity to hold the coil 150 and shallow cavities to hold electrical connections 154 are machined into a top wafer 206. Suitable machining techniques include, but are not limited to isotropic etching (e.g., wet etching), anisotropic etching (e.g. deep reactive ion etching), micro-sandblasting, laser ablation, and ultrasonic micro-machining. The machined surface of the top wafer 202 is (re-)polished to allow hermetic bonding with a bottom wafer 202.

Next, the coil 150 is inserted inside the deep cavity and two end wires are connected to feedthroughs inside the shallow cavities to form the electrical connections 154. The wires and coil 150 can connected using pressure compression bonding, wire bonding, gluing (with conductive glue), and direct soldering (with the use of an eutectic material that can be un-biocompatible). Once the coil 150 is positioned and connect properly, the bottom wafer 202 is bonded to the top wafer 206 using laser fusion bonding, pressure bonding, or low-temperature anodic bonding as described below. If necessary, the bottom wafer 202 and/or the top wafer 206 can be thinned in order to reduce the overall thickness of the stack. Those of skill in the art will readily appreciate that the coil 150 can disposed in other ways within the cavity and/or within other cavities; for example, the coil 150 can be wound against an interior wall of a cavity that houses an ASIC, capacitor, or other electronic component.

Fabricating Hermetically Sealed Feedthroughs

Fabrication of an electronics assembly, such as the one shown in FIG. 1, may begin with fabrication of a hermetically sealed feedthrough 112. Feedthroughs 112, apertures, cut lines, and other points are laid out on a substrate, such as a glass wafer, with a precision of about 1-10 µm. Next, the feedthroughs 112 and other apertures are drilled or etched into the substrate, which is then cut or diced into individual wafers like those shown in FIGS. 1, 2A, and 2B. The wafers are combined with other components and bonded together to form assemblies, which may be encapsulated in acrylic or any other suitable material.

Figure 5:
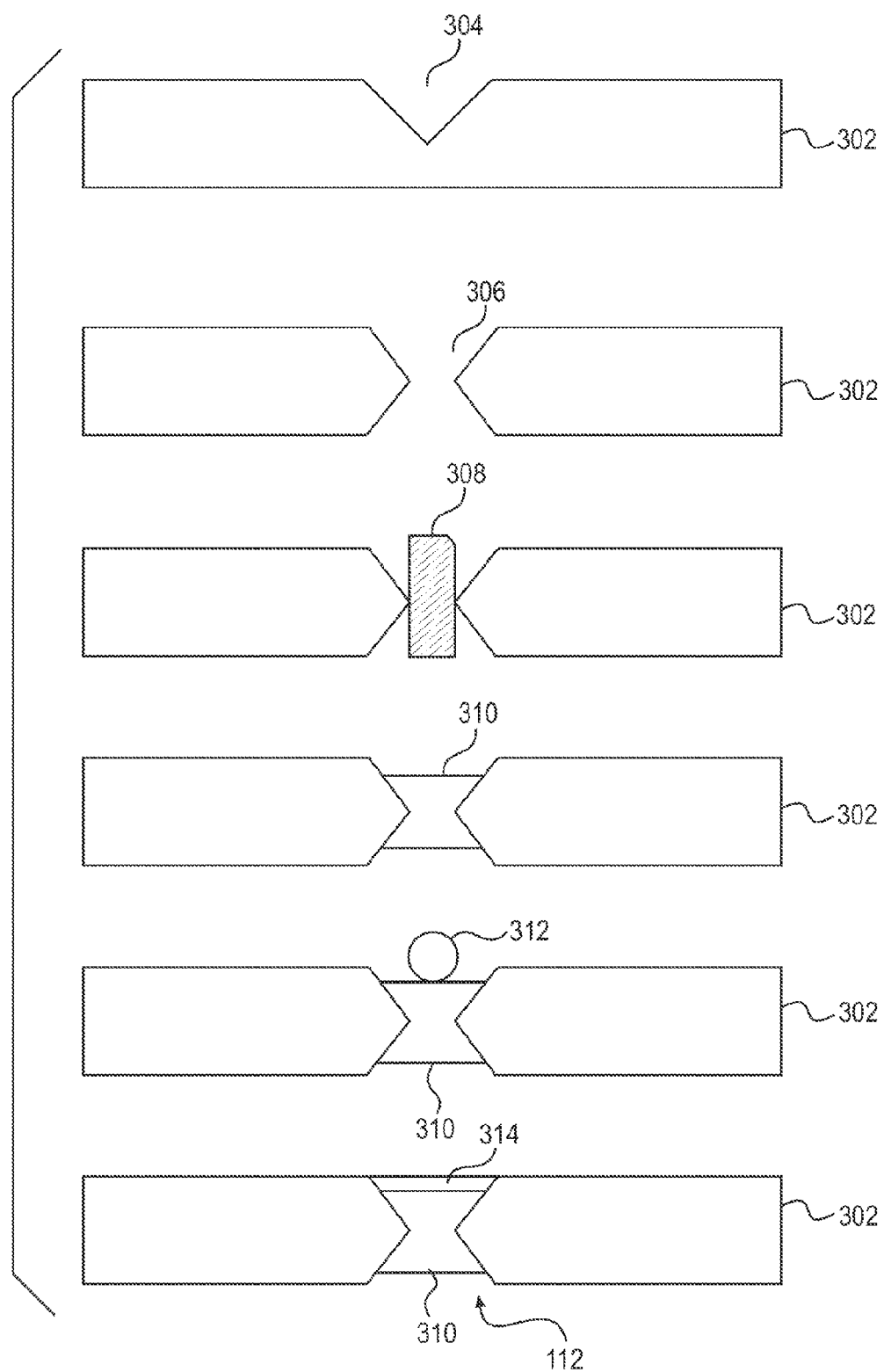
FIG. 5 illustrates the fabrication of a hermetically sealed feedthrough in a glass wafer.

FIG. 5 illustrates one technique for making hermetically sealed feedthroughs 112. Fabrication of the feedthrough 112 begins with drilling or etching a depression 304 into one side of a glass substrate 302, which may be borosilicate glass or any other suitable material. For example, the depression 304 can formed with by laser ablation (e.g., with an ultraviolet laser), micro-sandblasting, or ultrasonic micro-machining. The surface of the substrate 302 may be coated with a resist layer before drilling or etching for protection. The substrate 302 has a thickness of about 25-300 µm, or, more preferably, about 125-200 µm (e.g., about 175 µm). Next, another depression is drilled or etched into the other side of the substrate 302 to form a channel 306 that runs through the substrate 302. In some cases, the channel 306 is shaped roughly like an hourglass or diabolo, which is formed by placing together the small ends of two conical frustums. The channel 306 has a diameter of about 50-300 µm, or, more preferably, about 100-250 µm. Its average diameter may be about 200 (Alternatively, the channel 306 can be formed by simply continuing to drill or etch the first depression 302. This can result in a channel shaped like a conical frustum with a large opening on one side of the substrate 302 and a small opening on the other side of the substrate 302.)

Once the channel 306 is completed, conductive material 308 is deposited within the channel 306, e.g., by galvanic growth or electrochemical deposition. The conductive material 308 may be a biocompatible material, such as gold. Alternatively, the conductive material 308 may be a material, such as a nickel alloy (e.g., NiFe), whose coefficient of thermal expansion (CTE) is about equal to (e.g., within 10% of) the CTE of the substrate 302. In some instances, the CTEs of the conductive material 308 and the substrate may be about 2.0-5.0 ppm, e.g., 3.3 ppm. Matching the CTE of the conductive material 308 to the CTE of the substrate 302 reduces risks of leaks or implant deterioration caused by heating and/or cooling of the feedthrough 112 and the substrate 302 during manufacturing, testing, and sterilization of the implant. If the conductive material 308 is not biocompatible, the inner surface of the channel 306 may be coated or lined a biocompatible material to provide an extra layer of protection. For example, the channel 306 may be coated or lined with biocompatible titanium, then filled with conductive nickel.

Once completely deposited, the conductive material 308 forms a conductive path 310 that seals the channel 306 and provides electrical communication from one side of the substrate 302 to the other side of the substrate. (If necessary, the conductive material 308 and/or the substrate 302 is heated to seal the channel 306.) After the channel 306 is completely filled, any conducting base layer formed for galvanic growth is removed to prevent overgrowth.

The feedthrough 112 connects to other electrical components and/or connections via a biocompatible conductive layer 314 formed of gold, TiAu, or any other suitable biocompatible, conductive material. The layer 314 can be formed by placing a gold ball 312 in the channel aperture on one side of the conductive path, then heating or compressing the gold ball 312 to form the biocompatible conductive layer 314, which provides a low-resistance contact to the conductive path 310 that runs through the center of the feedthrough 112. If the melted or compressed gold is too thick, it can be polished to a desired thickness. In general, the thickness of the biocompatible conductive layer 314 determines its resistance and cost: thinner layers are less expensive, but tend to have higher resistance. In preferred embodiments, the biocompatible conductive layer 314 is about 10-200 µm thick (e.g., 100 µm thick) and has a resistance of about 10 Ohms or less.

FIGS. 6A and 6B show plan and perspective photographs, respectively, of a 3×3 matrix of feedthroughs 112 with NiFe conductive paths 310 and unpolished gold conductive layers 314 in a Borofloat® 33 substrate 302. Each feedthrough 112 has an hourglass shape with a length of about 150 µm to about 300 microns, with an average length of about 200 microns. The waist of the hourglass has a diameter of about 50 µm, and the ends of the hourglass have diameters of about 150 µm. The substrate 302 can be diced, cleaved, or otherwise separated into individual wafers used to form an electronics assembly.

Bonding Glass Wafers to Form Hermetically Sealed Cavities

As described above, glass wafers with feedthroughs can be bonded together to form hermetically sealed cavities using laser fusion bonding, pressure bonding, anodic bonding, or any other suitable bonding technique. Laser fusion bonding, or laser welding, is particularly attractive because it involves heating only those areas of the wafers that are in contact with each other. As a result, the components attached to and/or disposed between the wafers do not heat up during the fusion process. In addition, laser fusion bonding can be used to bond one piece of glass directly to another piece of glass (i.e., without layers between the pieces of glass), which eliminates additional materials and deposition steps.

Figure 7B:
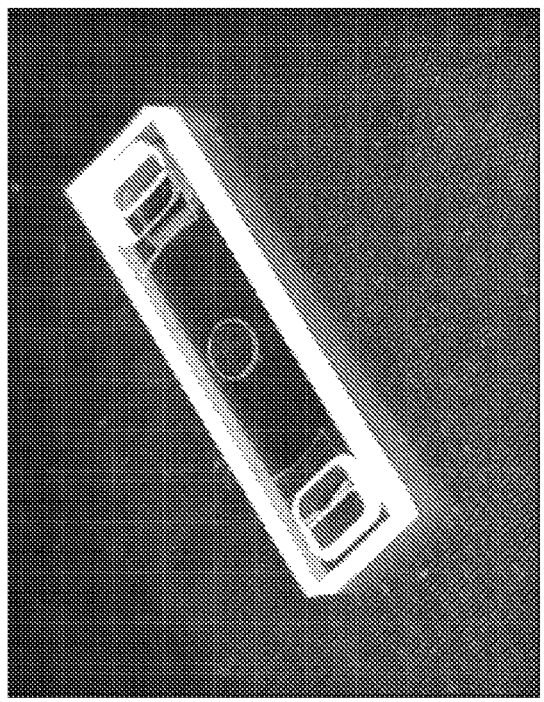
FIGS. 7A and 7B are photographs of glass wafers bonded together with laser fusion bonding to form hermetically sealed cavities that contain electronic components.
Figure 7A:
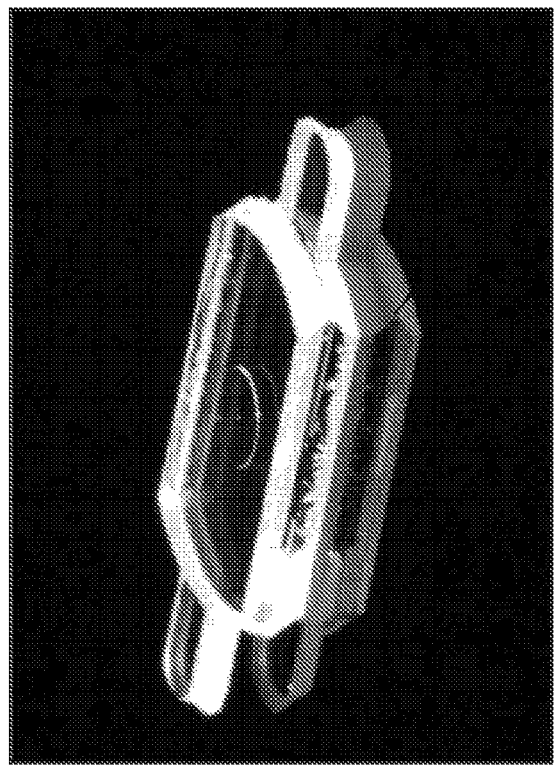

In laser fusion bonding, the wafers are held in contact with each other, and the beam from an ultrafast, ultraviolet laser is focused at or near the interface between the wafers. The laser emits picosecond or femtosecond pulses of light that heat the wafers, which causes the wafers to melt or fuse together. Scanning the pulsed laser beam in a closed loop along (or just inside) the edges of the wafers creates a hermetic seal between the wafers. The pulsed laser beam can also be scanned in multiple closed loops to create additional hermetically sealed areas within the perimeter of the wafers. For example, an ASIC may be sealed in a cavity, which itself is sealed within the perimeter of the device. FIGS. 7A and 7B are photographs of partially finished implants formed by scaling together glass wafers with laser fusion bonding.

Alternatively, wafers can be bonded together using pressure-compression bonding. A relatively thick ring of gold (e.g., about 50-250 µm, with an average of 200 µm) or other suitable material is deposited along the perimeter of at least of the wafers to be bonded. The wafers are aligned with each other, then compressed together. The compression causes the gold ring on the first substrate to soften and adhere to the second substrate (the ring may also flatten out or otherwise deform). The process temperature can be kept under 300° C., which is a critical temperature for certain components disposed on or between the wafers.

Figure 8:
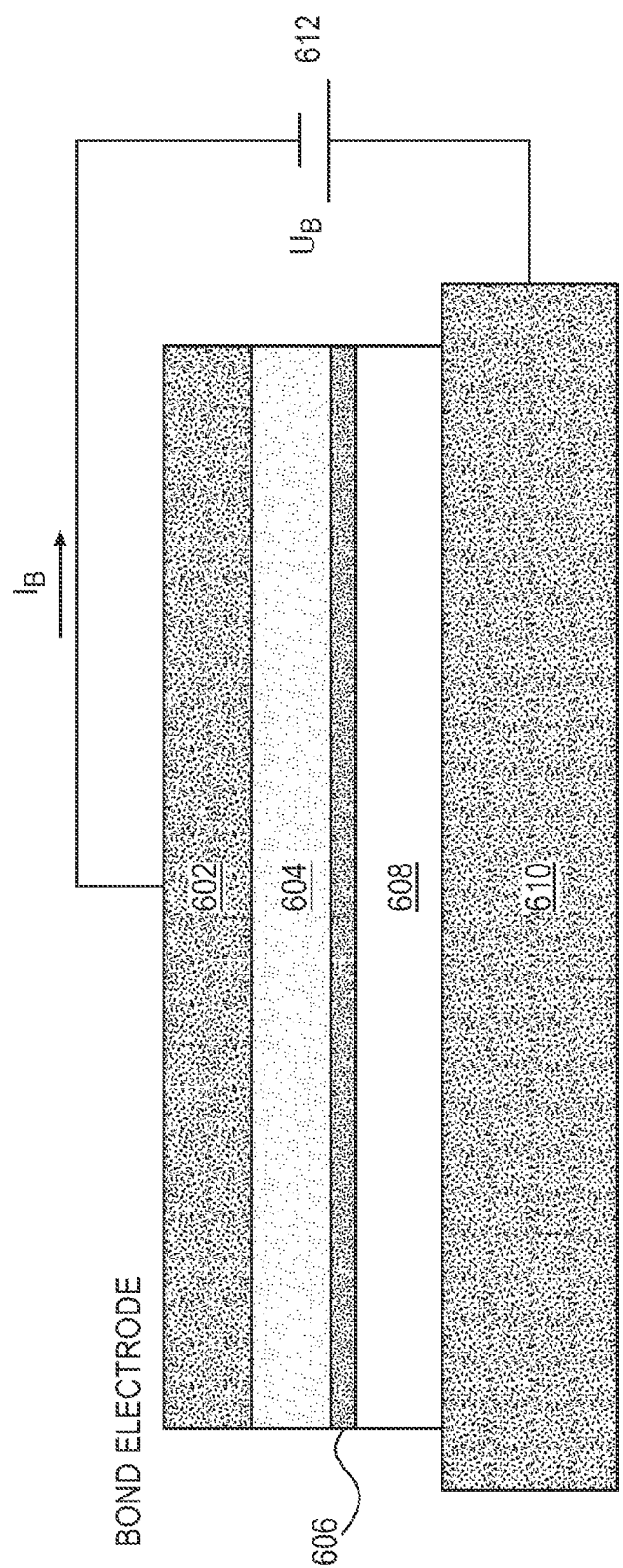
FIG. 8 illustrates anodic bonding of glass wafers to form a hermetically sealed cavity containing an electronic component.

Pairs of alkali-rich borosilicate glass wafers can also be bonded together using well-known, well-established low-temperature (e.g., under about 400° C.) anodic bonding techniques as shown in FIG. 8. First, one of the glass wafers to be bonded is coated with a thin layer 606 of silicon, polysilicon, tantalum, titanium, aluminum, and/or $SiN_x$ to form an coated glass wafer 608. The coated wafer 608 is cleaned (e.g., with isopropanol) and dried (e.g., with nitrogen gas), then aligned with an uncoated glass wafer 604 between a top tool 602 and a chuck 610, which are connected to a voltage source 612.

Setting the voltage $V_B$ of the voltage source 612 to several hundred Volts causes current $I_B$ to flow from the chuck 610 to the top tool 602 via the coated glass wafer 608, coating 606, and uncoated glass wafer 604. The current flow causes cations (e.g., alkali ions) in the glass wafers 604 and 608 to drift towards the top tool 602, which acts as a cathode, and anions in the glass wafers 604 and 608 to drift towards the chuck 610, which acts as an anode. (It also causes the wafer temperature to rise to about 280-350° C., e.g., about 300° C.) As a result, the region of the uncoated glass wafer 604 bordering the coating 606 becomes depleted of cations, and the region of the coated glass wafer 608 on the other side of the coating 606 becomes depleted of anions. This depletion causes the surfaces of the uncoated and coated glass wafers 604, 608 bordering the coating 606 to become highly reactive, which leads to the formations of a solid chemical bond between the wafers 604 and 608.

Testing Bonded Glass Wafers

Figure 10:
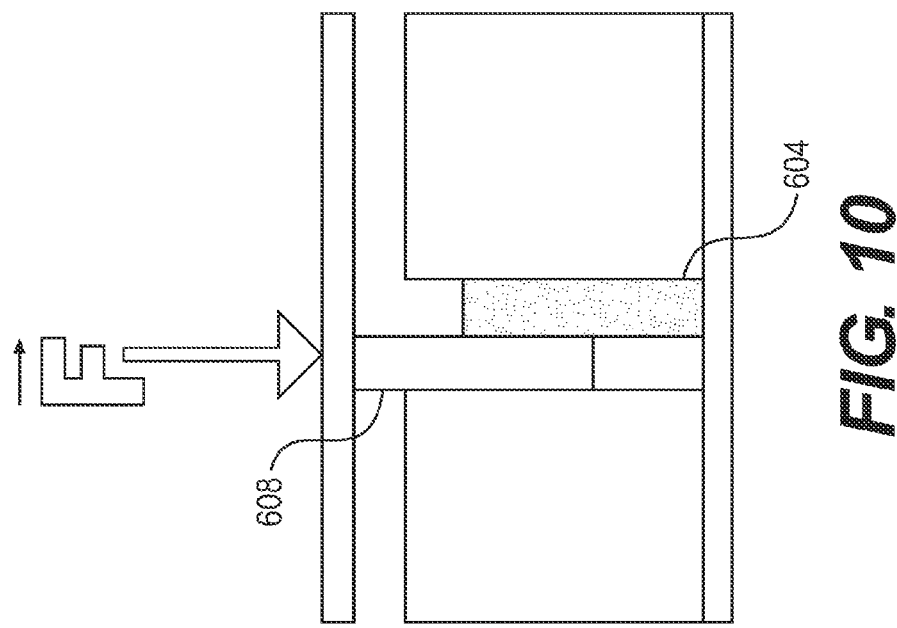
FIG. 10 illustrates a push test for measuring the bond strength of bonded wafers.
Figure 9:
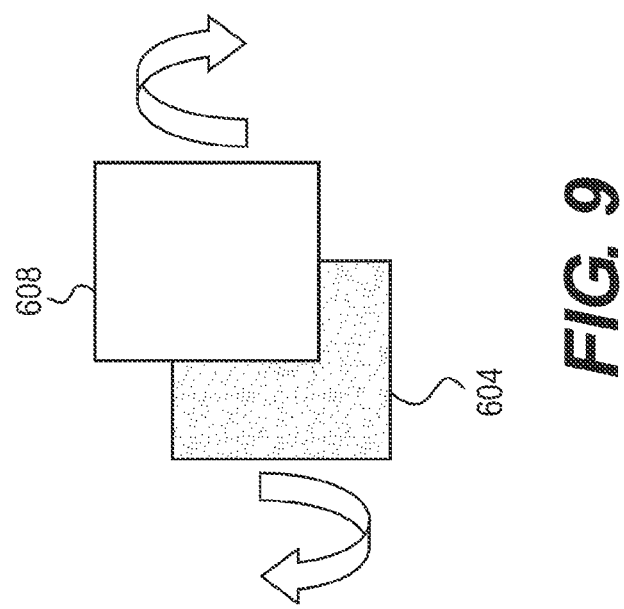
FIG. 9 illustrates a manual torsion test for measuring the bond strength of bonded wafers.

FIGS. 9 and 10 illustrate torsion and shear strength tests for measuring the strength of bonded glass wafers. In the torsion test, the bonded glass wafers (e.g., anodically bonded wafers 604 and 608) are twisted apart (i.e., as indicated by the arrows) by hand. In the shear strength test, the bonded glass wafers 604 and 608 are sheared apart by a force F applied along the plane of the interface between the wafers 604 and 608.

TABLE 1 shows results for torsion and shear strength tests of glass wafers bonded together using the anodic bonding technique described above with different bonding parameters and coatings. The tests were conducted using 500 µm thick, four-inch wafers of Borofloat® 33 borosilicate glass; in some cases, the wafers were diced into 10 mm×10 mm chips before testing. Each test was done at least one week after bonding to ensure sufficient relaxation of the bonded wafers. The results indicate that silicon, aluminum, and ITO/$SiN_x$ all offer relatively high strength with relatively low bonding temperatures.

TABLE 1

Strength Test for Anodically Bonded Glass Wafers

| Layer Material | Bonding Temp. (° C.) | Bonding Time (min) | Voltage (kV) | Manual Torsion | Push Test (N) | Observations |
|---|---|---|---|---|---|---|
| Silicon | 300 | 20 | 1.5 | Good | 100 | |
| Polysilicon | 300 | 20 | 1.5 | Good | | Partially Bonded; Glass Broken |
| | 400 | 2 | 1.0 | Good | 15 | Glass Broken |
| | 450 | 1 | 1.5 | Good | 40 | |
| Aluminum | 350 | 480 | 1.5 | Good | 30 | |
| | 450 | 1 | 1.0 | Good | 30 | |
| ITO/$SiN_x$ | 380 | 5 | 1.2 | Good | | Partially Bonded |
| | 450 | 10 | 1.5 | Good | 20 | |
| Tantalum | 400 | 2 | 1.5 | Good | 30 | |
| Titanium | 425 | 2 | 1.5 | Good | 35 | |
| | 450 | 1 | 1.5 | Good | 30 | |
| Ti/Al | 450 | 1 | 1.5 | Good | 20 | |

Sealing Liquid Crystal Material in Electro-Active Elements

Some embodiments of the implantable ophthalmic devices disclosed herein include electro-active cells that diffract, refract, and/or attenuate incident light in response to signals from a processor. For example, the assembly 100 shown in FIG. 1 includes an electro-active cell 160 actuated by one or both of the ASICs 130 disposed within hermetically sealed cavities 110 in the assembly 100. Exemplary electro-active cells should also be sealed to prevent electro-active fluid, such as liquid crystal material, from leaking into the eye or surrounding tissue.

Figure 11A:
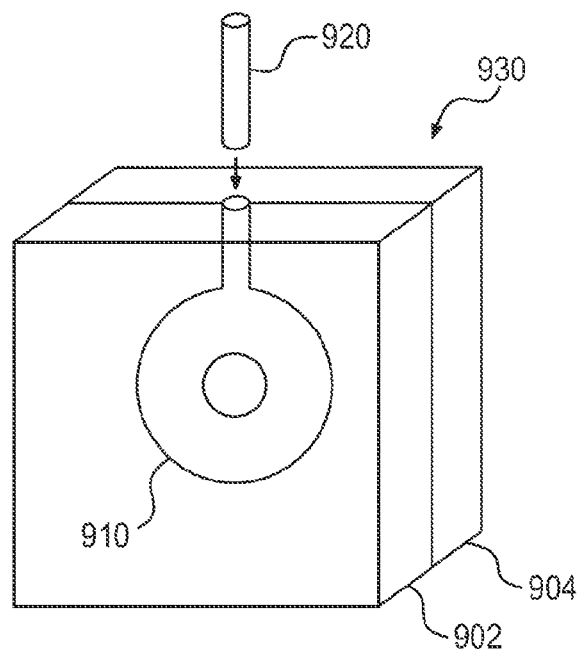
FIGS. 11A-11C illustrates filling a cavity in an electro-active element with liquid crystal material via a glass tube.
Figure 11B:
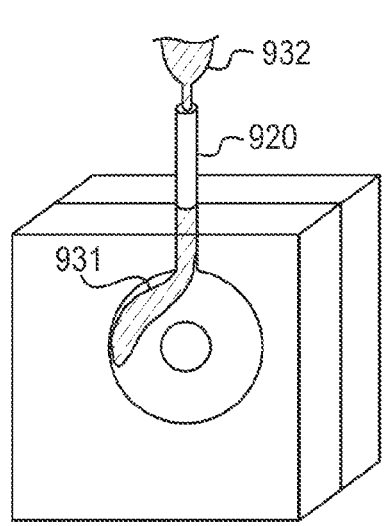
Figure 11C:
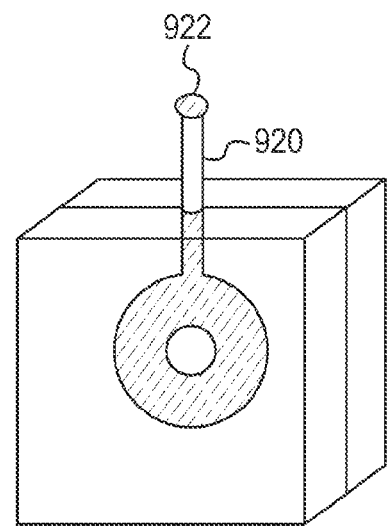

FIGS. 11A-11C show an exemplary technique for filling a cavity 910 with liquid crystal material 931 to form an electro-active element 930. First, the cavity 910 is created by bonding together a pair of glass substrates 902 and 904 using one of the bonding techniques described above. Instead of sealing the cavity 910, however, the manufacturer leaves a hole or aperture with a diameter of about 50-250 µm along one edge. A glass tube 920 whose outer diameter is barely smaller than the in inner diameter of the hole is inserted into the hole until it becomes wedged in the hole to form a tight seal as shown in FIG. 11A. If desired, the tube 920 may be heated to ensure that the tube 920 and hole are sealed together.

Liquid crystal material 931 is injected into the cavity 910 via a needle 932 inserted into the tube 920. The needle 932 has a pair of concentric walls that form two lumens: a central lumen that conveys the liquid crystal material 931 into the cavity 910 and an outer lumen that removes gas from the cavity 910. (Alternatively, the cavity 910 may have two holes: a first hole to inject the liquid crystal material and a second hole to evacuate gas displaced by the liquid crystal material.) Once the cavity 910 is filled with liquid crystal material 931, the glass tube 920 is sealed with a gold wire or tube 922 that is inserted into the glass tube 920, then heated to form a hermetic seal. If desired, excess portions of the glass tube 920 and the gold wire 922 can be removed and/or polished away.

Figure 12:
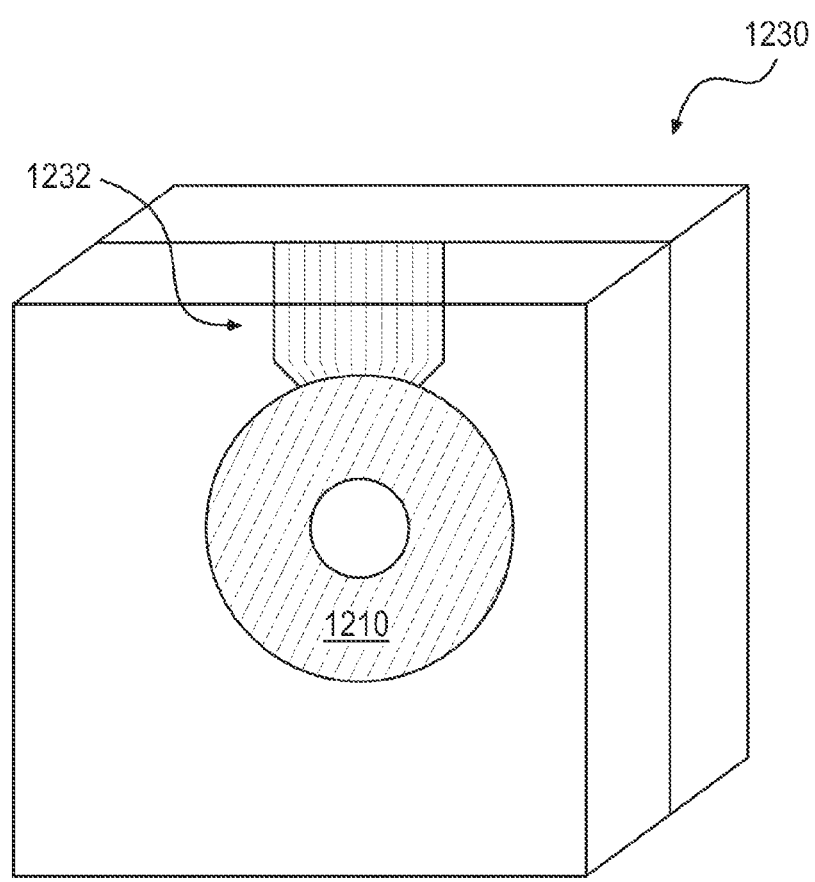
FIG. 12 illustrates filling a cavity in an electro-active element with liquid crystal material via an array of channels with textured interior surfaces.

FIG. 12 shows an alternative electro-active element 1230 that is filled with liquid crystal material via an array 1232 of microscopic channels. In some cases, the array 1232 may include hundreds to thousands of channels, each of which has a diameter of about 10-50 μm and provides a path for fluid communication between the edge of the electro-active element 1230 and a cavity 1210 in the interior of the electro-active element 1230. Liquid crystal material diffuses through some of the channels to the cavity and displaced gas flows out of the cavity via other channels. In some cases, the interior surfaces of the channels are modified, patterned, textured or otherwise patterned (e.g., through treatment with aminosilane, silanol, and/or other hydroxysilane derivatives) to reduce the surface energy of liquids flowing through the channel, thereby causing the liquid crystal material to fill the cavity 1210 more completely. Heat treatment (e.g., laser ablation, flame heating, or other surface heating) collapses the channels to form a hermetic seal that prevents the liquid crystal material from leaking out of the cavity.

Figure 13:
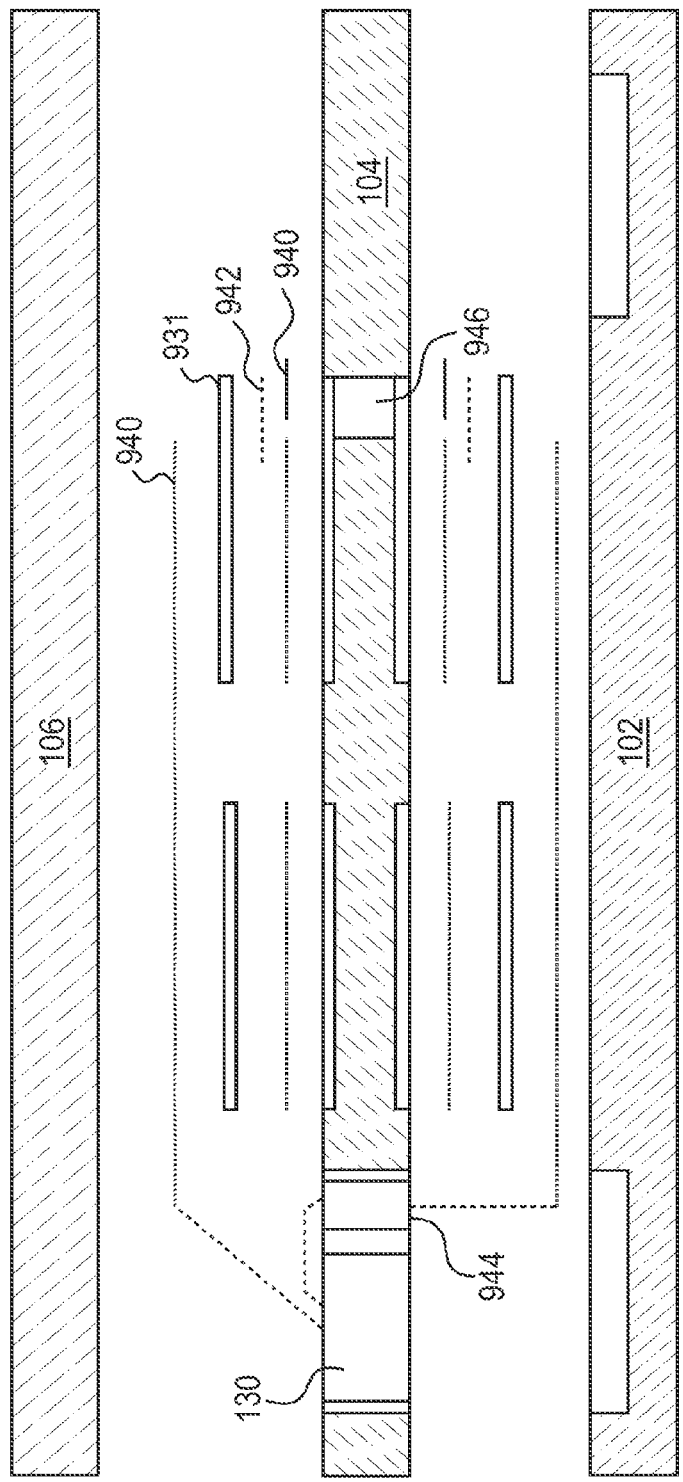
FIG. 13 shows an exploded profile view of an electro-active cell and its electrical connections.

FIG. 13 is an exploded profile view of a three-wafer electronics assembly, such as the assembly 100 shown in FIG. 1, that illustrates the electrical connections associated with the electro-active cell. Liquid crystal material 931 fills cavities on either side of an intermediate wafer 104, which is bonded to a top wafer 106 and a bottom wafer 102. Portions of the top and bottom wafers are coated with layers of ITO and $SiO_2$, which may be patterned or pixelated to form one or more electrodes for actuating the transmissivity or reflectivity of the electro-active cell as well understood in the art. A gold chip 944 running through the intermediate wafer 104 connects the layers of ITO and $SiO_2$ on the bottom wafer 202 to an ASIC 130 that controls the electro-active cell from within a hermetically sealed cavity. The layers of ITO and $SiO_2$ on the top wafer 206 connect directly to the ASIC 130. Layers of ITO and $SiO_2$ also cover sections of the intermediate wafer 104 to form additional electrodes, which are coupled electrically via a gold feedthrough 946 in the intermediate wafer 104.

Conformal Coating

FIGS. 14A and 14B show a bottom wafer 202 that is coated with a conformal coating 1402 that provides an additional layer of protection from cracks and fissures in the hermetic seal formed between bonded wafers. The coating 1402 prevents fluids from escaping a cavity via microcracks in the hermetic seal. A typical coating 1402 includes one or more layers of biocompatible and transparent materials, each of which has a thickness of about 100-300 nm, e.g., about 200 nm. For example, the coating 1402 may include two layers, each of which is about 150 nm thick. Many thin layers usually offer better protection than single thick layer. In addition to being biocompatible and transparent, coating materials should also be inert with respect to acrylic materials and the deposition processes used to make the implantable ophthalmic device. Suitable materials include silicon carbide (SiC), which can be formed into a diamond-like layer using high temperature deposition processes; silicon nitride ($Si_3N_4$), which has a low coefficient of thermal expansion, moderately high elastic modulus, and unusually high fracture toughness for a ceramic; and/or silica ($SiO_2$), which has good stability, is a very good dielectric, is well-known, and can be deposited using very well-established deposition processes.

CONCLUSION

A flow diagram is used herein. The use of flow diagrams is not meant to be limiting with respect to the order of operations performed. The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations.

However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.).

It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

The foregoing description of illustrative embodiments has been presented for purposes of illustration and of description. It is not exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

What is claimed is:

1. A method of making an implantable ophthalmic device, the method comprising:
   (a) placing an electronic component in electrical communication with a hermetically sealed feedthrough that provides a conductive path from a first side of a first substrate to a second side of the first substrate;
   (b) bonding a second substrate to the first side of the first substrate to at least partially define a hermetically sealed cavity containing the electronic component;
   (c) making an electro-active element by:
      (i) filling a cavity with liquid crystal material via a glass tube; and
      (ii) closing the glass tube to seal the liquid crystal material in the cavity; and
   (d) placing the electro-active element in electrical communication with the electronic component via the hermetically sealed feedthrough.

2. The method of claim 1 wherein (a) further comprises:
   creating a channel from the first side of the first substrate to the second side of the first substrate; and
   filling the channel with a conductive material to define the conductive path.

3. The method of claim 2 wherein the channel has a diameter of about 100 μm to about 250 μm.

4. The method of claim 3 wherein the coefficients of thermal expansion of the conductive material and the first substrate are about 2.0 ppm to about 5.0 ppm.

5. The method of claim 2 wherein (a) further comprises:
   forming a biocompatible conductive layer, in electrical communication with the conductive material, over an end of the channel.

6. The method of claim 3 further comprising:
   placing another electronic component in electrical communication with the electronic component via the biocompatible conductive layer and the conductive path.

7. The method of claim 1 further wherein (b) further comprises:
   fusion bonding the second substrate to the first side of the first substrate.

8. The method of claim 1 further wherein (b) further comprises:
   anodically bonding the second substrate to the first side of the first substrate.

9. The method of claim 1 further comprising:
   depositing a conformal coating about at least part of the hermetically sealed cavity to prevent leaks through cracks that may develop in the hermetically sealed cavity.

10. The method of claim 1 wherein the first substrate has a thickness of about 25 μm to about 300 μm.

11. A method of making an implantable ophthalmic device, the method comprising:
    (a) placing an electronic component in electrical communication with a hermetically sealed feedthrough that provides a conductive path from a first side of a first substrate to a second side of the first substrate;
    (b) bonding a second substrate to the first side of the first substrate to at least partially define a hermetically sealed cavity containing the electronic component;
    (c) making an electro-active element by:
       (i) filling a cavity with liquid crystal material via channels having modified interior surfaces; and
       (ii) collapsing the channels to seal the liquid crystal material in the cavity; and
    (d) placing the electro-active element in electrical communication with the electronic component via the hermetically sealed feedthrough.

12. The method of claim 11 wherein (a) further comprises:
    creating a channel from the first side of the first substrate to the second side of the first substrate; and
    filling the channel with an conductive material to define the conductive path.

13. The method of claim 12 wherein the channel has a diameter of about 100 μm to about 250 μm.

14. The method of claim 13 wherein the coefficients of thermal expansion of the conductive material and the first substrate are about 2.0 ppm to about 5.0 ppm.

15. The method of claim 12 wherein (a) further comprises:
    forming a biocompatible conductive layer, in electrical communication with the conductive material, over an end of the channel.

16. The method of claim 11 further wherein (b) further comprises:
    fusion bonding the second substrate to the first side of the first substrate.

17. The method of claim 11 further wherein (b) further comprises:
    anodically bonding the second substrate to the first side of the first substrate.

18. The method of claim 11 further comprising treating the channels with aminosilane, silanols, and/or hydroxysilane derivatives to create the modified interior surfaces.

19. The method of claim 11 further comprising:
    depositing a conformal coating about at least part of the hermetically sealed cavity to prevent leaks through cracks that may develop in the hermetically sealed cavity.

20. The method of claim 11 wherein the first substrate has a thickness of about 25 μm to about 300 μm.

* * * * *